(12) United States Patent
Phan et al.

(10) Patent No.: US 7,224,456 B1
(45) Date of Patent: May 29, 2007

(54) IN-SITU DEFECT MONITOR AND CONTROL SYSTEM FOR IMMERSION MEDIUM IN IMMERSION LITHOGRAPHY

(75) Inventors: Khoi Phan, San Jose, CA (US); Bhanwar Singh, Morgan Hill, CA (US); Bharath Rangarajan, Sunnyvale, CA (US); Ramkumar Subramanian, Sunnyvale, CA (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 401 days.

(21) Appl. No.: 10/858,759

(22) Filed: Jun. 2, 2004

(51) Int. Cl.
*G01N 15/02* (2006.01)

(52) U.S. Cl. ...................................... 356/338

(58) Field of Classification Search ..................... None
See application file for complete search history.

(56) References Cited

U.S. PATENT DOCUMENTS

2004/0238481 A1* 12/2004 Wang et al. ................... 216/2

* cited by examiner

*Primary Examiner*—Tu T. Nguyen
(74) *Attorney, Agent, or Firm*—Amin, Turocy & Calvin, LLP

(57) ABSTRACT

A system and method for detecting bubbles in a lithographic immersion medium and for controlling a lithographic process based at least in part on the detection of bubbles is provided. A bubble monitoring component emits an incident beam that passes through the immersion medium and is incident upon a substrate to produce a reflected and/or diffracted beam(s). The reflected and/or diffracted beam(s) is received by one or more optical detectors. The presence or absence of bubbles can be derived from information extracted by scatterometry from the reflected and/or diffracted beams. A process control component interacts with a positioning component and an optical exposure component to alter a lithographic process based at least in part on the results of the scatterometry.

15 Claims, 11 Drawing Sheets

IN-SITU DEFECT MONITOR AND CONTROL SYSTEM FOR IMMERSION MEDIUM IN IMMERSION LITHOGRAPHY

TECHNICAL FIELD

The present invention generally relates to semiconductor processing and, more particularly, to a system and method for detecting bubbles in an immersion medium and for optimizing an immersion lithographic process based at least in part on the detection of bubbles.

BACKGROUND OF THE INVENTION

In the semiconductor industry, there is a continuing trend toward higher device densities. To achieve these high device densities there have been, and continue to be, efforts toward scaling down device dimensions (e.g., at sub-micron levels) on semiconductor wafers. In order to accomplish such densities, smaller feature sizes and more precise feature shapes are required. This may include width and spacing of interconnecting lines, spacing and diameter of contact holes, and surface geometry, such as corners and edges, of various features. The dimensions of and between such small features can be referred to as critical dimensions (CDs). Reducing CDs and reproducing more accurate CDs facilitates achieving higher device densities.

High resolution lithographic processes are used to achieve small features. In general, lithography refers to processes for pattern transfer between various media. In lithography for integrated circuit fabrication, a silicon slice, the wafer, is coated uniformly with a radiation-sensitive film, the photoresist. The film is selectively exposed with radiation (e.g., optical light, x-ray, electron beam, etc.) through an intervening master template (e.g., mask, reticle, etc.) forming a particular pattern (e.g., patterned resist). Dependent upon coating type, exposed areas of the coating become either more or less soluble than unexposed areas in a particular solvent developer. More soluble areas are removed with the developer in a developing step, while less soluble areas remain on the silicon wafer to form a patterned coating. The pattern corresponds to either the image of the mask or its negative. The patterned resist is used in further processing of the silicon wafer.

The achievement of smaller critical dimensions is related to the resolution of the lithographic system. In particular, resolution can be defined as:

resolution=$k\lambda/NA$ where k is a lithographic constant, $\lambda$ is an exposure radiation wavelength, and NA is a numerical aperture. Numerical aperture is defined as a lens's ability to gather diffracted light and resolve fine details onto a substrate. Numerical aperture can be derived as follows:

$NA=n \sin \alpha$ where n is a refractive index and $2\alpha$ is an angle of acceptance of a lens. Refractive index is defined as a ratio of the speed of light in a vacuum to the speed of light in a particular medium.

From the above relationships, it can be seen that resolution can be increased by increasing refractive index and/or decreasing lithographic constant. Efforts to increase resolution and thereby reduce critical dimensions can be accomplished by several approaches. One approach involves the reduction in wavelength of the exposure radiation such as is achieved by moving from mercury g-line (436 nm), to excimer laser (193 nm), and further to 157 nm and extreme-ultraviolet (EUV) wavelengths. A second approach involves the utilization of resolution enhancement techniques such as phase-shifting masks. The use of phase shifting masks and off-axis illumination techniques have led to a reduction in the lithographic constant from about 0.6 to about 0.4. Finally, a third approach increases the numerical aperture through improvements in optical designs, manufacturing techniques, and metrology. Such improvements have lead to increases in numerical aperture from approximately 0.35 to greater than 0.7.

Immersion lithography provides another approach for increasing the resolution of an optical lithographic system and thereby achieving smaller critical dimensions. In immersion lithography, the gap between a substrate (e.g., wafer or reticle) and a final optical component (e.g., lens) is filled with an immersion medium which has a higher refractive index than the refractive index of air. Utilizing an immersion medium with a refractive index greater than that of air (approximately 1) increases numerical aperture. Increasing numerical aperture increases the resolution of an optical lithography system and thereby facilitates achievement of smaller critical dimensions. Furthermore, utilization of an immersion medium can decrease an effective wavelength of an exposure radiation propagating within the immersion medium without changing exposure sources, lasers, lens materials, etc.

Currently, immersion lithography is limited by various characteristics of immersion mediums and the immersion lithographic process. One significant problem encountered in immersion lithography is that most photoresists release gas upon exposure. Such released gases can form bubbles in the immersion medium. These bubbles can interfere with the exposure radiation resulting in scattered exposure light and potential processing defects in a substrate. Systems and methods which can detect bubbles in the immersion medium and accordingly alter processing can significantly improve the efficacy of immersion lithography systems and processes.

SUMMARY OF THE INVENTION

The following presents a simplified summary of the invention in order to provide a basic understanding of some aspects of the invention. This summary is not an extensive overview of the invention. It is intended to neither identify key or critical elements of the invention nor delineate the scope of the invention. Its purpose is merely to present some concepts of the invention in a simplified form as a prelude to the more detailed description that is presented later.

The present invention provides a system and method for detecting bubbles in a lithographic immersion medium and for controlling a lithographic process based at least in part on the detection of bubbles. In accordance with one aspect of the invention, an immersion medium occupies a gap between a final optical component and a substrate, and has an index of refraction greater than air. The immersion medium is nearly 100% transparent to an exposure wavelength. Additionally, according to another aspect of the present invention, the immersion medium can be water, oil, or other fluids suitable for immersion lithography.

According to one aspect of the present invention, a bubble monitoring component emits an incident beam that passes through the immersion medium and is incident upon a substrate to produce a reflected and/or diffracted beam(s).

The reflected and/or diffracted beam is received by one or more optical detectors. The reflected and/or diffracted beam contains information which can be analyzed to determine the presence or absence of bubbles in an immersion medium.

The present invention includes a bubble monitoring component comprising a detector component and a process control component. The detector component utilizes a light source that emits an incident beam that passes through the immersion medium and is incident upon the substrate to produce a reflected and/or diffracted beam(s). The detector component also utilizes an optical detector which can receive reflected and/or diffracted light. According to one aspect of the present invention, the presence or absence of bubbles can be derived from information extracted by scatterometry from the reflected and/or diffracted light. Scatterometry results produce an observed optical signature.

Another aspect of the present invention provides a method for controlling an immersion lithographic process based on the scatterometry results. A substrate with a known structure is immersed in an immersion medium. An incident light beam is emitted into the immersion medium and is incident on the substrate. Reflected and/or refracted beams are received by optical detectors and analyzed by scatterometry to determine the presence or absence of bubbles. According to one aspect of the present invention, a process control system can effectuate changes in a lithographic process by modifying the time between exposures in a step and repeat process, reposition the substrate prior to exposure, exchange the immersion medium, etc., based at least in part on the presence or absence of bubbles in the immersion medium. A process control component interacts with a positioning component and an optical exposure component to alter the lithographic process based at least in part on the results of the scatterometry (i.e. the optical signature)

In accordance with another aspect of the present invention, simulation and modeling is used to determine expected optical signatures for the presence of bubbles at various locations within the immersion medium. A data store is utilized to store a library of optical signatures. According to another aspect of the present invention, the system pattern matches observed optical signatures to the simulated and/or actual observed optical signatures stored in a library and thereby determines the location of any bubbles within the immersion medium.

To the accomplishment of the foregoing and related ends, certain illustrative aspects of the invention are described herein in connection with the following description and the annexed drawings. These aspects are indicative, however, of but a few of the various ways in which the principles of the invention may be employed and the present invention is intended to include all such aspects and their equivalents. Other advantages and novel features of the invention will become apparent from the following detailed description of the invention when considered in conjunction with the drawings.

DETAILED DESCRIPTION OF THE INVENTION

Figure 1:
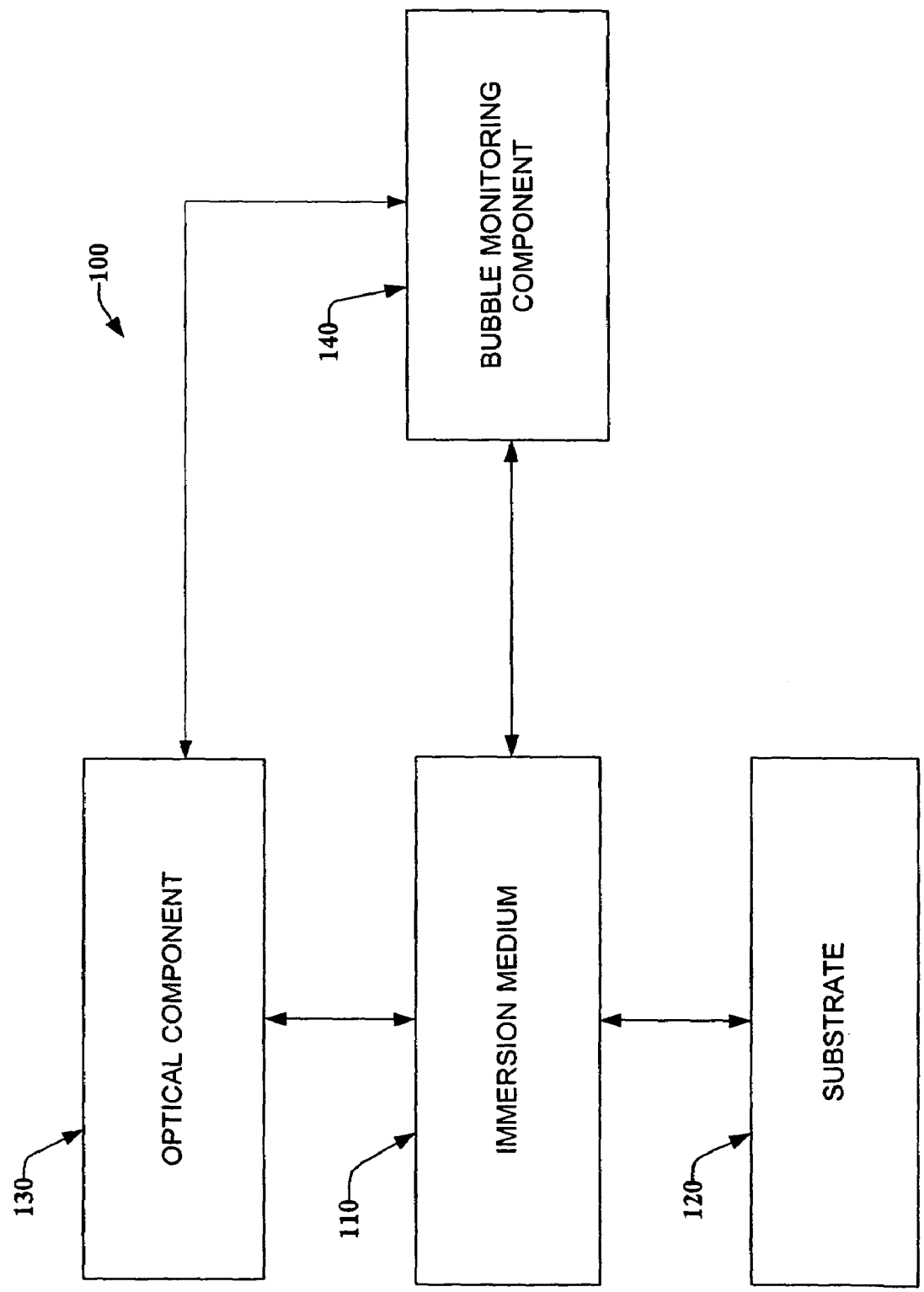
FIG. 1 is an illustration of a block diagram of a system in accordance with an aspect of the present invention for detecting bubbles in an immersion medium utilized in an immersion lithographic process.

The present invention is now described with reference to the drawings. In the following description, for purposes of explanation, numerous specific details are set forth in order to provide a thorough understanding of the present invention. It may be evident, however, to one skilled in the art that one or more aspects of the present invention may be practiced with a lesser degree of these specific details. In other instances, known structures and devices may be shown in block diagram form in order to facilitate describing one or more aspects of the present invention. The following detailed description is of the best mode presently contemplated by the inventors for practicing the invention. It should be understood that the description of these aspects are merely illustrative and that they should not be taken in a limiting sense.

As used in this application, the term "component" is intended to refer to a computer-related entity, either hardware, a combination of hardware and software, software, or software in execution. For example, a component may be, but is not limited to being a process running on a processor, a processor, an object, an executable, a thread of execution, a program, a set of co-operating computers and/or processes and a computer. The term "bubble" as used in this application is intended to refer to any foreign object in an immersion medium which can block, reflect, diffract or otherwise interfere with light that passes through the immersion medium.

It is to be appreciated that various aspects of the present invention can employ technologies associated with facilitating unconstrained optimization and/or minimization of error costs. Thus, non-linear training systems/methodologies (e.g., back propagation, Bayesian, fuzzy sets, non-linear regression, or other neural networking paradigms including mixture of experts, cerebella model arithmetic computer (CMACS), radial basis functions, directed search networks, and function line networks) can be employed. The invention can employ various inference schemes and/or techniques in connection with state determination, inference and/or prediction. As used herein, the term "inference" refers generally to the process of reasoning about or inferring states of the system, environment, and/or user from a set of observations as captured via events and/or data. Inference can be employed to identify a specific context or action, or can generate a probability distribution over states, for example. The inference can be probabilistic—that is, the computation of a probability distribution over states of interest based on a consideration of data and events. Inference can also refer to techniques employed for composing higher-level events from a set of events and/or data. Such inference results in the construction of new events or actions from a set of observed events and/or stored event data, whether or not the events are correlated in close temporal proximity, and whether the events and data come from one or several event and data sources. Various classification schemes and/or systems (e.g., support vector machines, neural networks, expert systems, Bayesian belief networks, fuzzy logic, data fusion engines, etc.) can be employed in connection with performing automatic and/or inferred action in connection with the subject invention.

FIG. 1 illustrates a block diagram of a system 100 for detecting bubbles in an immersion medium utilized in an immersion lithographic process in accordance with an aspect of the present invention. The immersion medium 110 occupies the gap between a substrate 120 (e.g., wafer, reticle, etc.) and an exposure optical component 130 (e.g., lens). Characteristics of the immersion medium 110 can include low optical absorption at the exposure radiation wavelength, compatibility with resist and lens material, uniformity of properties throughout the immersion medium 110, non-contaminating, etc. According to an aspect of the present invention, the immersion medium 110 can be, for example, water, oil (e.g., perfluorinated polyethers (PFPE) including PFPE-K, PFPE-Y, PFPE-D, PFPE-M, PFPE-Z), etc.

The immersion medium 110 utilized in connection with the present invention has a refractive index greater than the refractive index of air. Refractive index is a ratio of speed of light in a vacuum to speed of light in a particular medium and refractive index varies dependent upon radiation wavelength. For example, the refractive index corresponding to 193 nm wavelength radiation is approximately 1.4 for water and approximately 1 for air. It is desirable to have an immersion medium with a refractive index greater than 1 provided that the immersion medium is 100% transparent to the exposure radiation wavelength as a refractive index greater than 1 allows for production of features with smaller critical dimensions However, the invention is not intended to be limited to 100% transparent immersion medium with refractive index greater than 1 as various other percentage transparencies are contemplated and intended to fall within the scope of the hereto appended claims.

Immersion medium 110 interacts with a bubble monitoring component 140. Bubble monitoring component 140 monitors immersion medium 110 for the presence of bubbles. Often the resist layer of a substrate will give off a gas when the surface of the resist comes in contact with the immersion medium. Bubble monitoring component 140 is operatively coupled to optical component 130. If bubble monitoring component 140 detects the presence of bubbles, the bubble monitoring component can inhibit or otherwise affect the lithographic exposure of substrate 120 by optical component 130. If the bubble monitoring component does not detect the presence of bubbles, then the lithographic exposure may proceed as programmed. It is to be appreciated that bubble monitoring component 140 can comprise, for example, a scatterometry component. The present invention contemplates any suitable bubble monitoring component 140 and/or system, and such components and/or systems are intended to fall within the scope of the hereto-appended claims.

It is further to be appreciated that information gathered by bubble monitoring component 140 can be utilized for generating feedback and/or feed-forward data that can facilitate achieving effective lithographic exposure of substrate 120. The system 100 for monitoring and/or controlling bubbles in the immersion medium 110 can additionally employ such data to control components and/or operating parameters associated with an immersion lithographic process. For instance, feedback/feed-forward information can be generated in connection with the system to increase the time interval between successive exposures in conjunction with a step and repeat system thereby allowing sufficient time for bubbles from a previous exposure to dissipate. Similarly, such information may be used to reposition a substrate prior to lithographic exposure or to cause the replacement of the immersion medium.

Figure 2:
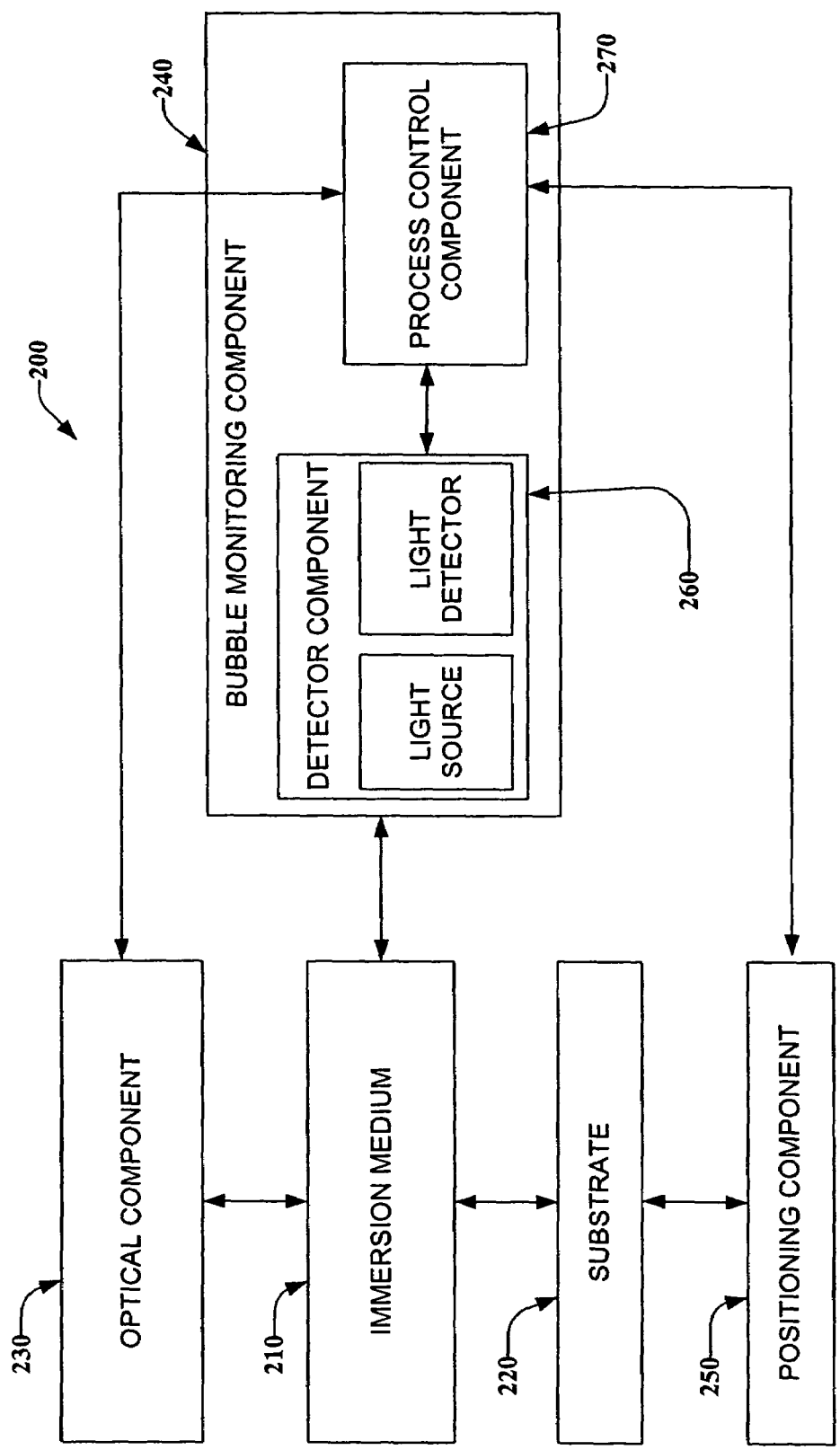
FIG. 2 is an illustration of a block diagram of a system for detecting bubbles in a lithographic immersion medium and for controlling a lithographic process based at least in part on the detection of bubbles in accordance with an aspect of the present invention.

FIG. 2 illustrates an example of a system 200 for detecting bubbles in a lithographic immersion medium 210 and for controlling a lithographic process based at least in part on the detection of bubbles in accordance with an aspect of the present invention. System 200 comprises an immersion medium 210, a substrate 220, an optical component 230, a bubble monitoring component 240, and a positioning component 250. Immersion medium 210 can possess a refractive index greater than 1 to facilitate lowering an effective wavelength of exposure radiation propagating within immersion medium 210 from optical component 230. For example, the immersion medium 210 can be water, oils or other suitable immersion fluids. Optical component 230, such as a lens, can be employed to emit light to expose substrate 220 (e.g., a wafer) via immersion medium 210, thereby effectuating a particular semiconductor fabrication process, such as, for example, wafer etching. Immersion medium 210 is further operatively coupled to bubble monitoring component 240.

Bubble monitoring component 240 comprises a detector component 260 and a process control component 270. Detector component 260 is operative to detect the presence of bubbles in immersion medium 210. Detector component 260 comprises a light source and a light detector. The light source emits an incident beam onto substrate 220 (e.g., wafer, wafer stage, reticle, etc.). The combination of features existing on substrate 220 is a known structure. When the incident beam is emitted, it interacts with substrate 220 and immersion medium 210 and the incident beam is reflected and/or diffracted as one or more reflected and/or diffracted beams. The light detector further comprises one or more photodetectors comprising a spectrometer or other suitable device for detecting and analyzing reflected and/or diffracted beam(s) from substrate 220 and from bubbles within immersion medium 210. In accordance with one aspect of the present invention, the presence or absence of bubbles in immersion medium 210 is determined based on characteristics of the reflected and/or diffracted beam(s), properties of the immersion medium, and the known structure of the substrate. Those skilled in the art will understand and appreciate various other non-destructive optical measurement techniques that could be utilized.

Process control component 270 is operatively coupled to lithographic optical component 230, to positioning component 250 and to detector component 260. In accordance with one aspect of the present invention, process control component 270 is programmed and/or configured to control operation of detector component 260, optical component 230, and positioning component 250. Positioning component 250 is coupled to substrate 220 and facilitates the movement and positioning of substrate 220 for successive exposures from optical component 230 as part of a step and repeat lithographic process.

According to one particular aspect of the present invention, process control component 270 controls detector component 260 so that an incident beam selectively evaluates immersion medium 210 at a known location on substrate 220 with a known structure. Furthermore, the timing of the evaluation of immersion medium 210 is managed by process control component 270. For example, the incident beam can be emitted to selectively evaluate the immersion medium 210 just after positioning component 250 completes adjusting the position of substrate 220 and just prior to a planned exposure by the optical component 230.

Additionally, process control component 270 utilizes information obtained by detector component 260 from an evaluation of immersion medium 210 to alter characteristics of the immersion lithographic process thereby facilitating optimization of the immersion lithographic process. Process control component 270 controls optical component 230, positioning component 250, detector component 260 and immersion medium 210 to alter the immersion lithographic process based at least in part on the information obtained from the evaluation. By way of illustration and not limitation, process control component 270 may delay the exposure provided by optical component 230 until bubbles are no longer detected, may cause positioning component 250 to reposition substrate 220 to a new position further removed from the source of bubbles (e.g. a prior exposure locations), or may cause immersion medium 210 to be removed and replaced.

Figure 3:
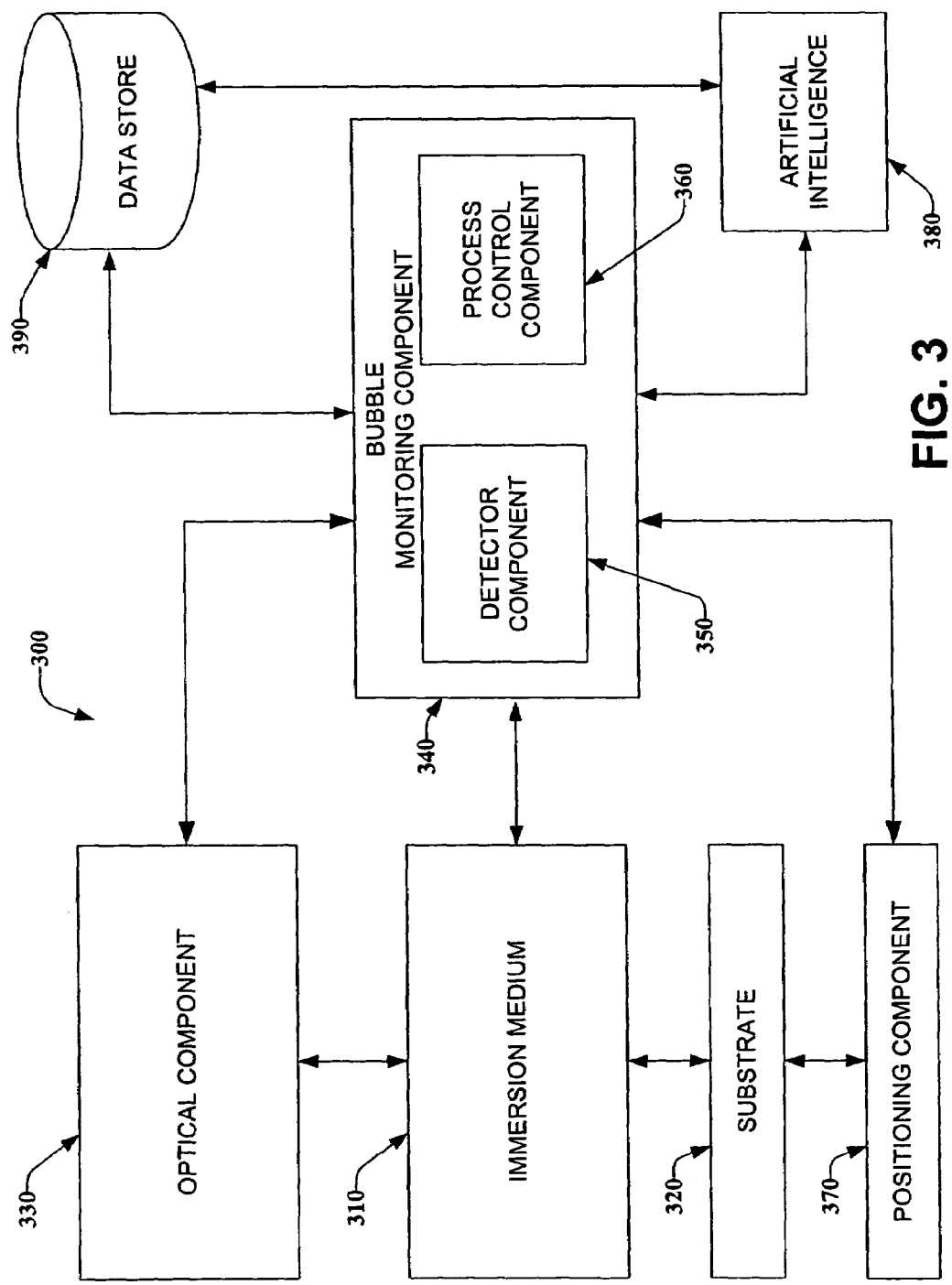
FIG. 3 is an illustration of a block diagram of another system for detecting bubbles in a lithographic immersion medium and for controlling a lithographic process based at least in part on the detection of bubbles in accordance with an aspect of the present invention.

FIG. 3 illustrates an example of another system, 300, for detecting bubbles in a lithographic immersion medium and for controlling a lithographic process based at least in part on the detection of bubbles in accordance with an aspect of the present invention. System 300 can employ various inference schemes and/or techniques in connection with detecting bubbles in the immersion medium and correspondingly controlling an immersion lithographic process. As used herein, the term "inference" refers generally to the process of reasoning about or inferring states of the system, environment, and/or user from a set of observations as captured via events and/or data. Inference can be employed to identify a specific context or action, or can generate a probability distribution over states, for example. The inference can be probabilistic—that is, the computation of a probability distribution over states of interest based on a consideration of data and events. Inference can also refer to techniques employed for composing higher-level events from a set of events and/or data. Such inference results in the construction of new events or actions from a set of observed events and/or stored event data, whether or not the events are correlated in close temporal proximity, and whether the events and data come from one or several event and data sources. Various classification schemes and/or systems (e.g., support vector machines, neural networks, expert systems, Bayesian belief networks, fuzzy logic, data fusion engine, etc.) can be employed in connection with performing automatic and/or inferred action in connection with the subject invention.

Referring again to FIG. 3, system 300 comprises an immersion medium 310 (e.g., water, oil, etc.) that possesses a refractive index greater than 1, facilitating lowering an effective wavelength of an exposure radiation. An optical component 330, such as a lens, is employed to emit light toward a substrate 320 (e.g., wafer, reticle, etc.) via immersion medium 310, thereby effectuating a particular semiconductor fabrication process such as, for example, wafer etching. A bubble monitoring component 340 is operatively coupled to immersion medium 310. Bubble monitoring component 340 comprises a detector component 350 and a process control component 360. Bubble monitoring component 340 is operatively coupled to optical component 330 and to a positioning component 370 that is operative to position substrate 320 within immersion medium 310. Further, bubble monitoring component 340 is operatively coupled to an artificial intelligence (AI) component 380 that is capable of making inferences regarding system operation and to a data store 390. Data store 390 stores data corresponding to known structures on substrates 320, various immersion medium characteristics, prior replacement of immersion medium 310, optical signatures for various immersion mediums with and without the presence of bubbles, etc. Additionally, AI component 380 is operatively coupled to data store 390. According to one aspect of the present invention, AI component 380 determines optimal changes for the immersion lithographic process which can be effectuated by process control component 360. Furthermore, AI component 380 and/or bubble monitoring component 340 store and retrieve data from data store 390 corresponding to immersion medium 310 such as, for example, refractive index values, lithographic constant values, presence or absence of bubbles under a given set of conditions, amount of time required for bubbles to dissipate, prior replacement of immersion medium 310, etc. These examples are given by way of illustration only and are not in any way intended to limit the scope of the present invention or the number of ways, or manner in which AI component 380 makes inferences.

Figure 4:
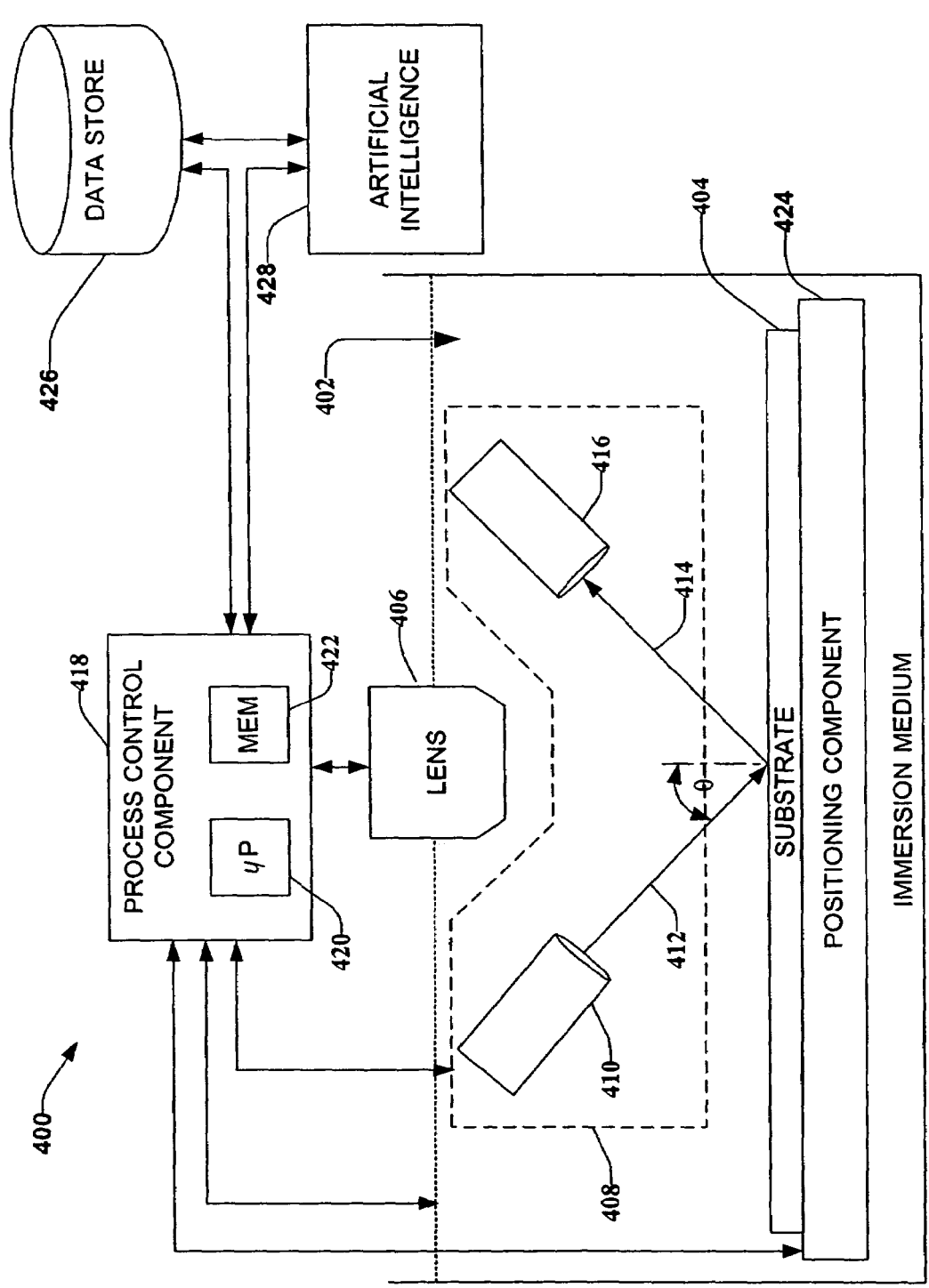
FIG. 4 is an illustration of another system for detecting bubbles in a lithographic immersion medium and for controlling a lithographic process based at least in part on the detection of bubbles in accordance with an aspect of the present invention.

FIG. 4 illustrates an example of another system, 400, for detecting bubbles in a lithographic immersion medium 402 and for controlling a lithographic process based at least in part on the detection of bubbles in accordance with an aspect of the present invention. As part of system 400, a substrate 404 with a known structure is located within immersion medium 402. An optical component, such as a lens 406, is also at least partially within immersion medium 402. In accordance with an aspect of the present invention, system 400 utilizes detector component 408 for detecting bubbles within immersion medium 402. Detector component 408 is a non-destructive component that includes a light source 410 and a light detector 416. By way of illustration, light source 410 is one or more optical emitters that emit an incident light beam 412 toward substrate 404 at an incident angle $\theta$ relative to a normal reference line. Light source 410 is a frequency stabilized laser; however it is understood that any suitable light source (e.g., laser diode, helium neon (HeNe)

gas laser, halogen lamp, UV light sources, E-UV light sources, etc.) can be utilized in connection with the present invention. At least a portion of incident beam 412 is reflected and/or diffracted from the surface of substrate 404 and/or from bubbles within the immersion medium as a reflected beam 414. One or more optical detectors 416 receive the reflected and/or diffracted beam 414.

System 400 further comprises a process control component 418. Process control component 418 is operative to change the configuration of detector component 408 so as to evaluate the entire volume, or alternatively a selected portion of the entire volume of immersion medium 402. By way of example, and not as limitation, such configuration change can include changing the direction of light source 410 such that light is emitted in a different direction and by making a corresponding change, if necessary, in the alignment of detectors 416 for detection of reflected and/or diffracted light. The process of configuration changes followed by evaluation is repeated until the entire desired volume of the immersion medium has been evaluated.

Optical detector(s) 416 are operative to analyze characteristics of the reflected beam 414 and are operative to discern characteristics of light reaching the optical detectors. As described below, the light reaching the optical detectors contains information about the immersion medium through which the light has traveled and about the substrate from which the light is reflected and/or refracted. By way of example, optical detector 416 includes a spectrometer or other instrument capable of providing spectrally-resolved information regarding reflected beam 414. The portion of the reflected and/or diffracted beam 414 that enters optical detector 416 for analysis is determined at least in part by the reflection/diffraction characteristics of the immersion medium and the known wafer structure along with properties of optical detector 416 and any associated optical elements used in conjunction with optical detector 416.

Optical detector 416 collects light passing through immersion medium 402 that is reflected and/or diffracted by features on substrate 404. Optical detector 416 also collects light which reflects and/or diffracts off bubbles within the immersion medium before entering the optical detector. Bubble monitoring component 408 can determine the presence of bubbles in the immersion medium 402 by comparing characteristics such as wavelength, phase and/or intensity of the light received at various locations within optical detector 416 to set of reference characteristics determined when bubbles were not present in the immersion medium. The location at which the reflected and/or diffracted light is received along with the wavelength, intensity and/or phase of the reflected and/or diffracted light received at optical detector 416 changes based on the presence or absence of bubbles within immersion medium 402.

Process control component 418 further comprises a processor 420 and memory 422. Memory 422 stores program code executed by processor 420 for carrying out operating functions of the system. Memory 422 also serves as a storage medium for temporarily storing information from system 400. Memory 422 can be volatile memory or nonvolatile memory, or can comprise both volatile and nonvolatile memory. By way of illustration, and not limitation, nonvolatile memory can comprise read only memory (ROM), programmable ROM (PROM), electrically programmable ROM (EPROM), electrically erasable ROM (EEPROM), or flash memory. Volatile memory can comprise random access memory (RAM), which acts as external cache memory. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM). The memory of the present systems and methods is intended to comprise, without being limited to, these and any other suitable types of memory.

In accordance with one aspect of the present invention, process control component 418 facilitates operation of an immersion lithographic process. According to this aspect of the present invention, process control component 418 is operatively coupled to immersion medium 402, lens 406, bubble monitoring component 408, positioning component 424, a data store component 426, and a artificial intelligence component 428. Process control component 418 can effectuate changes in an immersion lithographic process such as, for example, a delay in starting an exposure through lens 406, a repositioning of substrate 404, a replacement of immersion medium 402, etc., based at least in part upon information obtained from bubble monitoring system 408. By comparing location and characteristics of light received by optical detector 416 to acceptable locations and reference characteristics stored in either RAM or data store 426, system 400 can determine whether the immersion medium contains bubbles which will interfere with the exposure of substrate 404. Process control component 418, in conjunction with artificial intelligence component 428, utilizes the results of the comparison to determine a next appropriate action. For example, it may determined that more time is required for bubbles to dissipate before allowing the exposure of substrate 404 from lens 406, that positioning system 424 needs to reposition substrate 404 to a new location prior to exposure from lens 406, or that immersion fluid 402 needs to be replaced prior to proceeding with a next step in an immersion lithographic process.

In accordance with another aspect of the present invention, the presence or absence of bubbles within an immersion fluid can be determined utilizing scatterometry techniques. Scatterometry is a technique for extracting information about a surface upon which an incident light has been directed. Information concerning properties including, but not limited to, dishing, erosion, profile, chemical composition, thickness of thin films and critical dimensions of features present on a surface such as a substrate can be extracted. Furthermore, information about an immersion medium through which light is transmitted can be extracted by utilizing scatterometry techniques. The intensity and/or the phase of a reflected and/or diffracted beam of light will change based on properties of the surface upon which the light is directed and the immersion medium through which the light travels. Information can be extracted by evaluating the wavelength, phase and/or intensity of light received at various locations of a detector. In accordance with one aspect of the present invention, the presence of bubbles within an immersion fluid can be determined utilizing scatterometry techniques.

Figure 5:
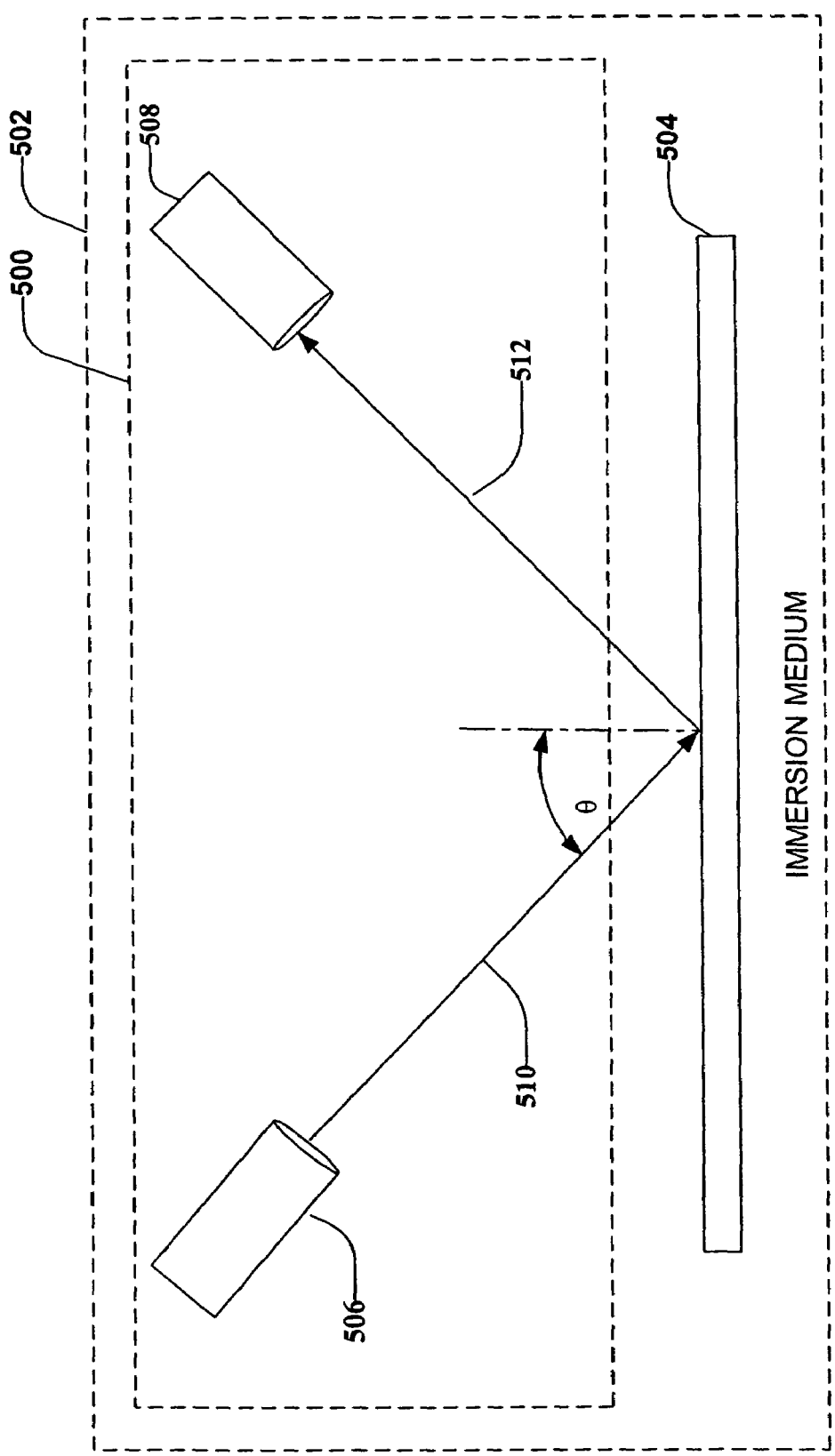
FIG. 5 is an illustration of a detector component in accordance with an aspect of the present invention.

FIG. 5 is an illustration of a detector component 500 in accordance with an aspect of the present invention. In FIG. 5, detector component 500 is completely immersed in immersion medium 502. It is understood that detector component 500 may be completely immersed within immersion medium 502 or may be only partially immersed within immersion medium 502. It is also possible that detector component 500 may not be immersed within immersion medium 502 at all, but that only light emitted and detected by detector component 500 travels within immersion medium 502. Immersion medium 502 can be water, oil, or any other fluid suitable for exposure of substrate 504 via an immersion lithographic process.

Detector component 500 is comprised of light source 506, such as one or more optical emitters. Light source 506 is the source of incident light beam(s) 510 emitted toward substrate 504 at an incident angle θ relative to a normal reference line. Light source 506 is a frequency stabilized laser; however it is understood that any suitable light source (e.g., laser diode, or helium neon (HeNe) gas laser, halogen lamp, mercury lamp, UV light source, E-UV light source, etc.) can be utilized in connection with the present invention. At least a portion of incident beam 510 is reflected and/or diffracted off substrate 504 as reflected and/or diffracted beam 512.

Detector component 500 is further comprised of one or more optical detectors 508 that receive the reflected and/or diffracted beam 512 and further operate to determine characteristics of light reaching the detectors. As described below, information can be extracted from the light reaching the optical detectors about the immersion medium through which the light has traveled and about the substrate from which the light is reflected and/or diffracted.

Optical detector 508 includes a spectrometer or other instrument capable of providing spectrally-resolved information concerning the reflected and/or diffracted beam 512. The portion of the reflected and/or diffracted beam 512 that enters optical detector 508 for analysis is determined at least in part by the reflection/diffraction characteristics of the immersion medium 502 and substrate 504 along with properties of optical detector 508 and any associated optical elements used in conjunction with optical detector 508.

Optical detector 508 collects light passing through immersion medium 502 that is reflected and/or diffracted by features built upon the substrate 504. Further, optical detector 508 also collects light which reflects and/or diffracts off bubbles within the immersion medium before entering the optical detector. Detector component 500 can be utilized with other components to determine the presence of bubbles in the immersion medium 502 by comparing wavelength, phase and/or intensity of the light received at various locations within optical detector 508 to known set of reference wavelength, phase and/or intensity characteristics at corresponding locations within optical detector 508. The location, wavelength, intensity and/or phase of the reflected and/or diffracted light received at optical detector 508 will change based on the presence of bubbles within the immersion medium 502. This is illustrated in more detail in FIG. 6.

Figure 6:
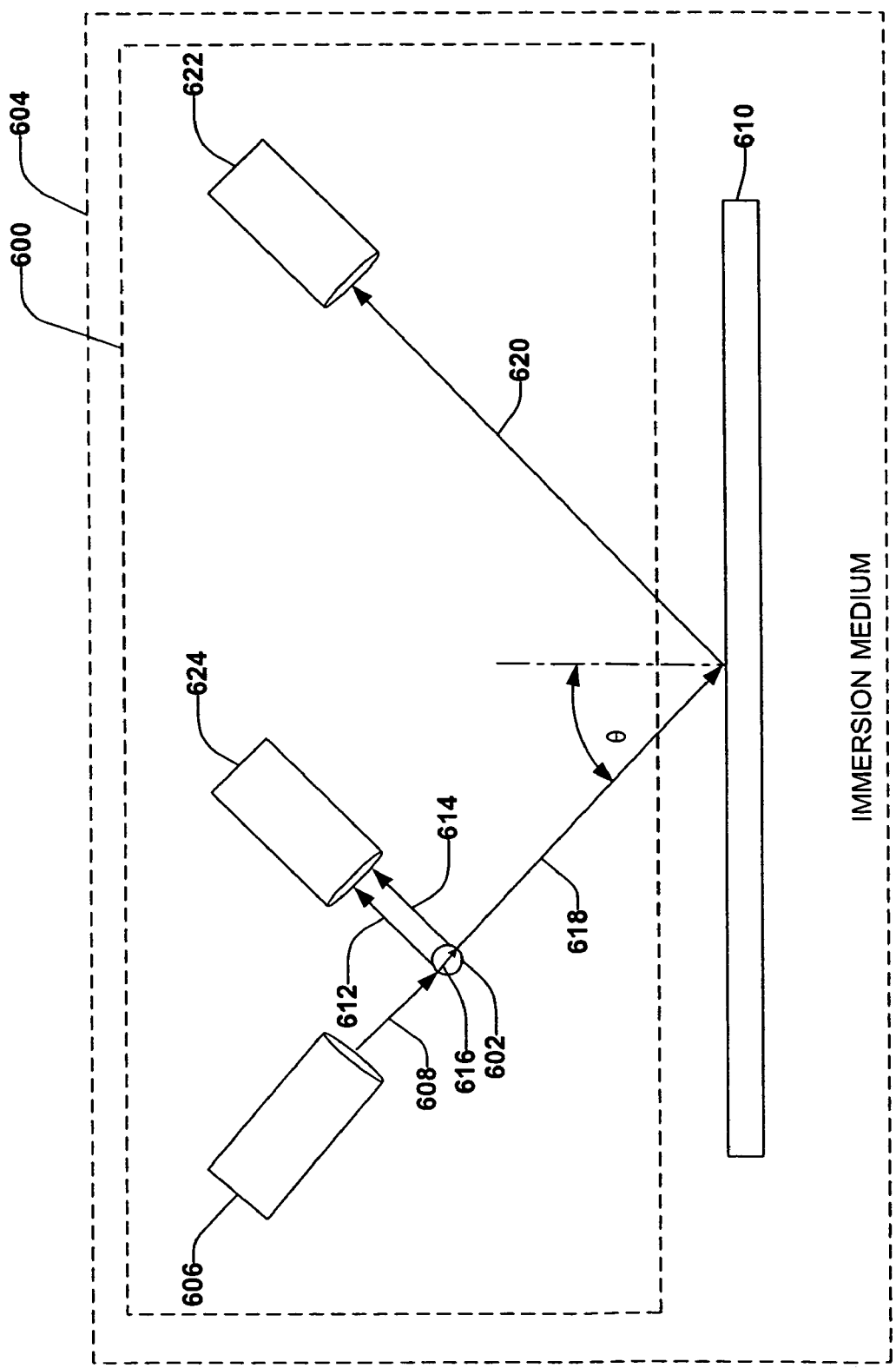
FIG. 6 is an illustration of a detector component in accordance with an aspect of the present invention.

FIG. 6 is an illustration of another detector component, 600, in accordance with an aspect of the present invention. In FIG. 6, bubble 602 exists within immersion medium 604. Although a translucent bubble is used for purposes of illustration, it is understood that 602 may be any contaminant or other object in the immersion medium that interferes with light passing through the immersion medium. Light source 606 is the source of incident light beam(s) 608 emitted toward substrate 610 at an incident angle θ relative to a normal reference line. However, prior to reaching substrate 610, light beam 608 is incident on bubble 602. Upon encountering bubble 602, incident beam 608 is reflected and/or diffracted as the light enters the bubble at a first surface and again as light exits bubble 602 from a second surface. Reflected beam 612 represents light reflected from the first surface of bubble 602 and reflected beam 614 represents light reflected from the second surface of bubble 602. Diffracted beam 616 passes through bubble 602 from the first surface to the second surface. Diffracted beam 618 exits bubble 600 from the second surface and continues on to be incident upon wafer 610 at an incident angle θ relative to a normal reference line. At least a portion of diffracted beam 618 is reflected and/or diffracted off substrate 618 as reflected beam 620. One or more optical detectors 622, 624 receive the light beams 612, 614 and 620. Optical detectors 622 and 624 include a spectrometer or other instrument capable of providing spectrally-resolved information concerning the light beams 612, 614 and 620. Optical detectors 622 and 624 analyze characteristics of the light beams 612, 614, and 620 and operate to discern characteristics of light reaching the optical detectors. Optical detectors 622 and 624 analyze wavelength, intensity, phase and other characteristics of the reflected and/or diffracted beams received at various locations.

In reference to FIG. 5 and FIG. 6, if light sources 506 and 606 emit light with identical characteristics (wavelength, phase, intensity, etc.) upon identical substrates at identical incident angles, in identical immersion mediums, the characteristic of reflected and/or diffracted beam 512 as received by optical detector 508 will differ from the characteristics of reflected and/or diffracted beam 620 as received by optical detector 622 as a result of the presence of bubble 602. By determining the characteristics of light received by the optical detectors and comparing the results to known reference characteristics and conditions, the presence or absence of bubbles can be determined.

Scatterometry is a technique for extracting information about a surface upon which an incident light has been directed. Information concerning properties including, but not limited to, dishing, erosion, profile, chemical composition, thickness of thin films and critical dimensions of features present on a surface such as a wafer can be extracted. Furthermore, information about an immersion medium through which light is transmitted can be extracted by utilizing scatterometry techniques. The location at which the reflected and/or diffracted light is received along with the wavelength, intensity and/or phase of the reflected and/or diffracted light will change based on properties of the surface upon which the light is directed and the immersion medium through which the light travels. Information can be extracted by determining and evaluating the characteristics of the light received at various locations of an optical detector. In accordance with one aspect of the present invention, the presence of bubbles within an immersion fluid can be determined utilizing scatterometry techniques.

The presence or absence of bubbles at different positions within an immersion medium will have varying effects on the wavelength, intensity and/or phase of light passing through the immersion medium depending upon the position of the bubbles within the immersion medium. Analysis by scatterometry or other similar techniques results in a substantially unique set of characteristics (i.e. a signature) for a given condition. When the reflected and/or diffracted beams are analyzed by scatterometry, a signature generated as a result of the detected location, wavelength, intensity, phase, etc. can be pattern matched, for example, to a library of signatures to determine whether the observed signature corresponds to a reference signature stored within the signature library. The signature library can be populated from prior observed signatures and/or signatures generated by modeling and simulation. Thus, in accordance with an aspect of the present invention, a determination can be made concerning the presence or absence of bubbles present in an immersion medium utilized in connection with a known structure on a substrate by pattern matching an observed signature to a library of signatures.

A signature for known ideal conditions associated with a particular spot on a particular substrate in a particular immersion medium containing no bubbles can be observed and stored in a library stored within a data store or memory. In accordance with one aspect of the present invention, this known good signature is used as a reference signature against which actual observed signatures are compared for purposes of determining whether bubbles are present. Similar signatures may be observed for known "bad" conditions when one or more bubbles may be present at one or more positions within the immersion medium.

In accordance with another aspect of the present invention, simulation and modeling can be employed to produce signatures for the library against which observed signatures can be matched. For example, for a given spot on a substrate, a simulation can provide an expected signature when no bubbles are present in the immersion medium. Similarly, through simulation and modeling, an expected signature can be produced for the presence of a bubble at any specific location within the immersion medium. Similarly, the simulation and modeling can provide the expected signature for any number of bubbles at virtually any locations within the immersion medium. In accordance with another aspect of the present invention, signatures obtained through simulation and modeling can be combined with prior observed signatures to form the signature library. In accordance with another aspect of the present invention, by matching a real-time observed signature to a known condition reference signature produced either by actual observation or through simulation and modeling, the location and number of bubbles within an immersion medium can be determined. In accordance with yet another aspect of the present invention, a system can determine whether or not to alter a lithographic process, based at least in part upon such information.

Figure 7:
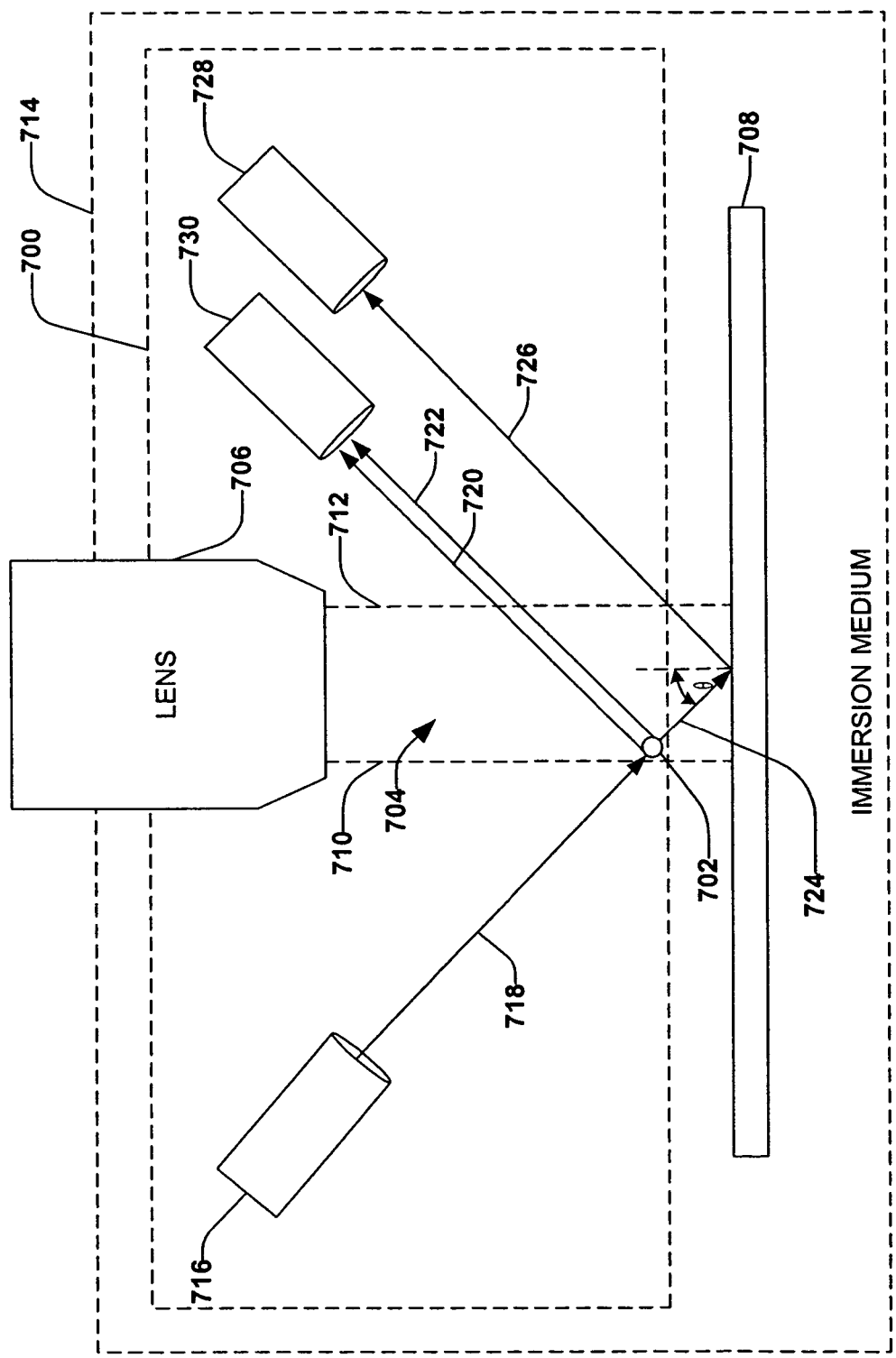
FIG. 7 is an illustration of a detector component in accordance with an aspect of the present invention for detecting bubbles within an immersion medium.

FIG. 7 is an illustration of another detector component, 700, in accordance with an aspect of the present invention for detecting bubbles within an immersion medium. FIG. 7 illustrates the presence of a bubble 702 at a location known to cause problems with a lithographic exposure of a substrate. Bubble 702 exists within the path of an exposure beam 704 emitted by a lens 706. Lens 706 emits light beam 704 to expose a layer of resist deposited on a substrate 708. The outer edges of exposure beam 704 are defined by 710 and 712. Bubble 702 exists within immersion medium 714 and lies directly between lens 706 and substrate 708 such that at least a portion of exposure beam 704 can not reach substrate 708 without encountering bubble 702. The presence of bubble 702 in this location will result in an improper exposure of substrate 708.

Prior to exposure of substrate 704 by lens 706, detector component 700 is utilized to evaluate the conditions of the immersion medium. Light source 716 emits light beam 718 in a direction to be incident on substrate 708 at angle θ to a normal. Light beam 708 encounters bubble 702 from which light is reflected and/or diffracted prior to reaching substrate 708. Light beam 720 is reflected and/or diffracted from a first surface of bubble 702 and light beam 722 is reflected and/or diffracted from a second surface of bubble 702. Diffracted beam 724 exits bubble 702 and continues on to be incident upon wafer 708. At least a portion of beam 724 is reflected and/or diffracted from the surface of substrate 708 as beam 726. Optical detectors 728 and 730 operate to detect the location, wavelength, intensity and phase of beams 720, 722 and 726. Optical detectors 728 and 730 comprise scatterometry or other similar components that determine an observed signature for the given condition. The observed signature is then pattern matched against a library of signatures whereby it is matched to a signature determined when a bubble substantially similar to bubble 702 existed at substantially the same position within a substantially similar immersion medium. Based on the results of the pattern match, the presence of bubble 702 at the illustrated position between lens 706 and substrate 708 is detected. Based at least in part upon this information, a system can alter a lithographic process by, for example, delaying exposure until bubble 702 has subsided, repositioning wafer 708 to a new position, exchanging the immersion medium 714, or other similar actions.

Figure 8:
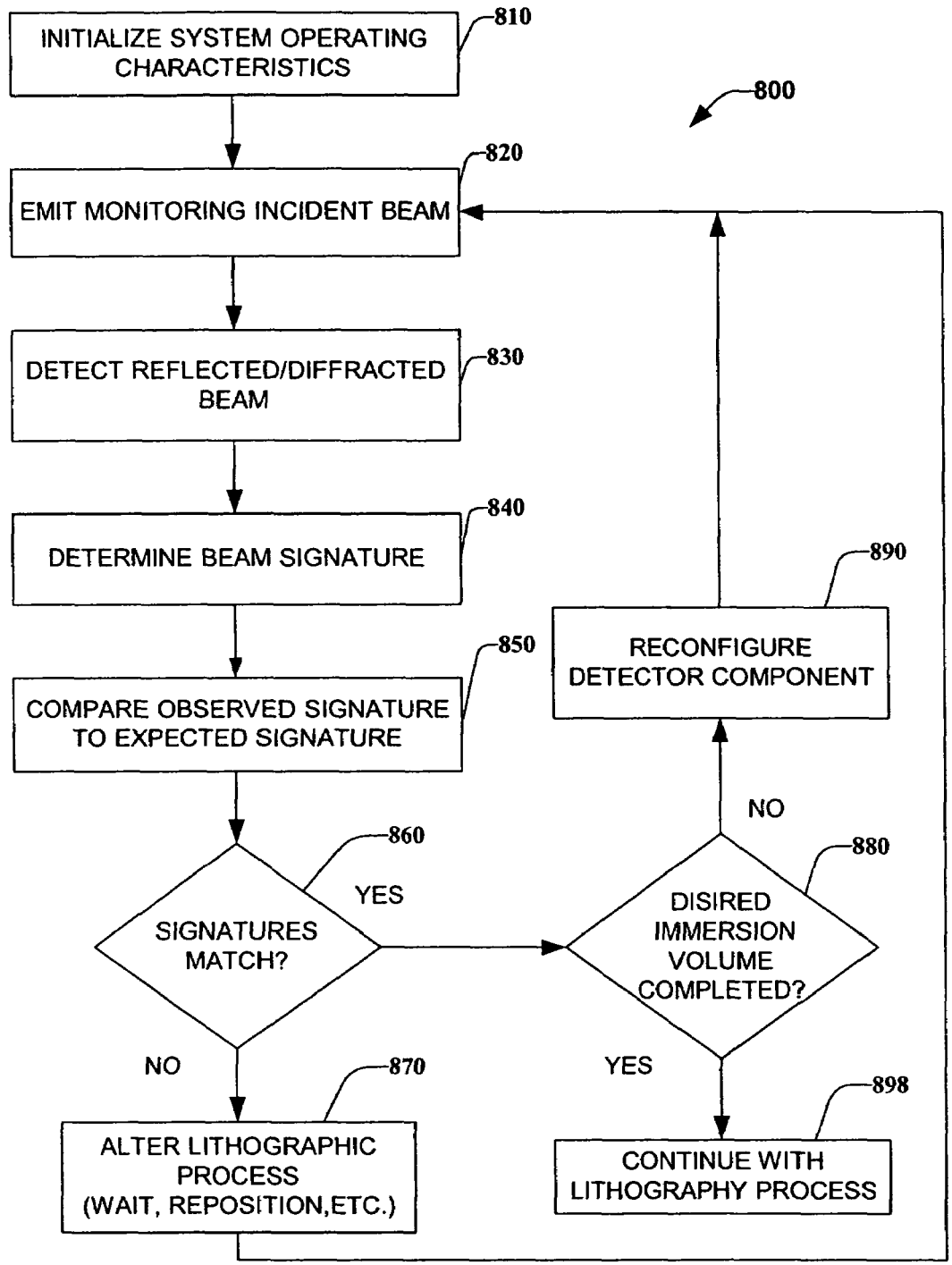
FIG. 8 is an illustration of a methodology to monitor an immersion medium for the presence of bubbles in accordance with an aspect of the present invention.
Figure 9:
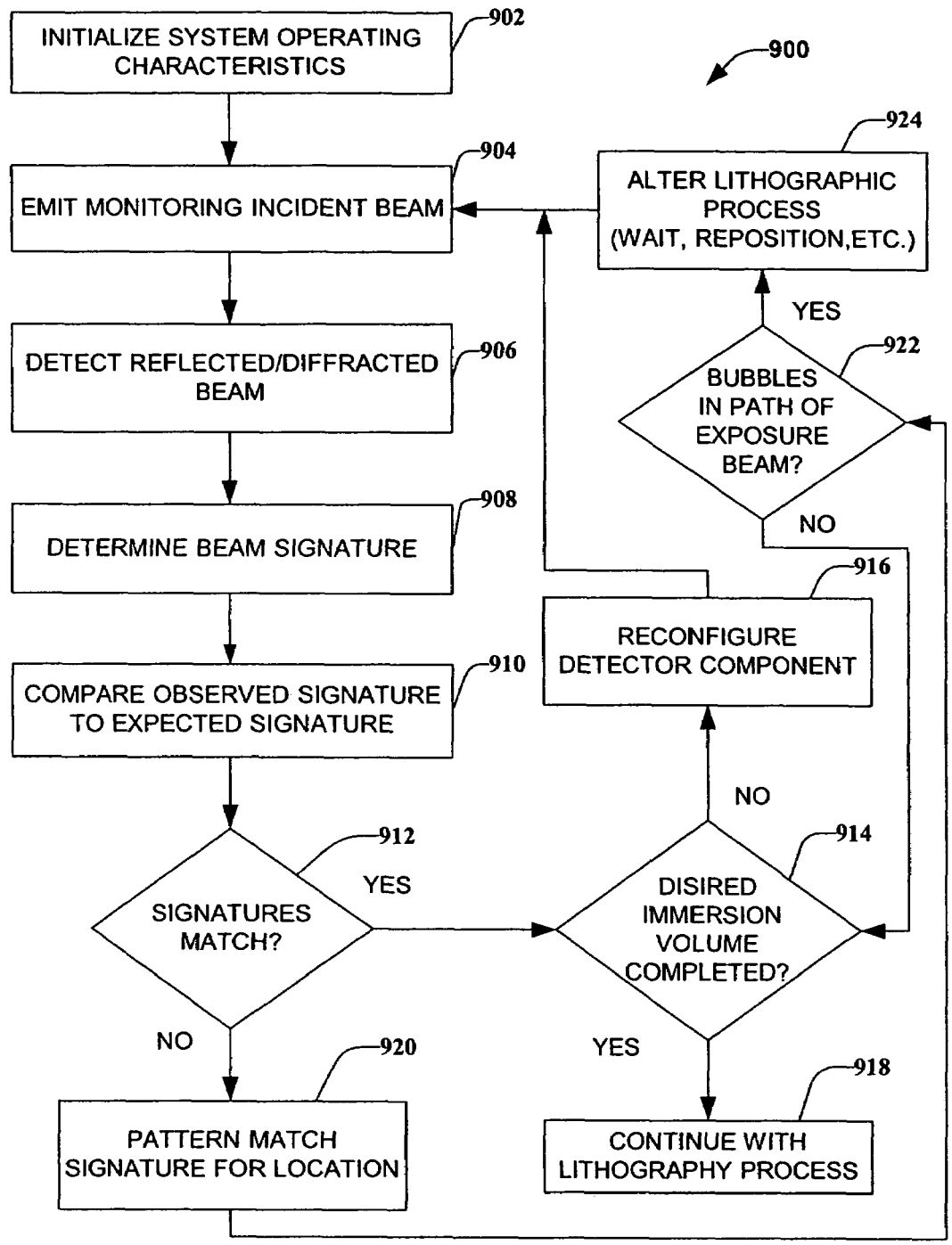
FIG. 9 is a flow diagram illustrating a methodology in accordance with an aspect of the present invention for determining the location of bubbles within an immersion medium, and then selecting an alternative action, based at least in part, upon the location of any bubbles.

In view of the exemplary systems shown and described above, methodologies 800 and 900, which may be implemented in accordance with the present invention, will be better appreciated with reference to the flow diagrams illustrated in FIG. 8 and FIG. 9. While, for purposes of simplicity of explanation, the methodologies 800 and 900 are shown and described as a series of function blocks, it is to be understood and appreciated that the present invention is not limited by the order of the blocks, as some blocks may, in accordance with the present invention, occur in different orders and/or concurrently with other blocks from that shown and described herein. Moreover, not all illustrated blocks may be required to implement a methodology in accordance with the present invention. It is to be appreciated that the various blocks may be implemented via software, hardware, a combination thereof, or any suitable means (e.g., device, system, process, component, etc.) for carrying out the functionality associated with the blocks. It is also to be appreciated that the blocks are merely to illustrate certain aspects of the present invention in a simplified form and that these aspects may be illustrated via a lesser and/or greater number of blocks.

FIG. 8 is an illustration of a methodology to monitor an immersion medium for the presence of bubbles. The methodology provides for a lithographic process to continue if no bubbles are present and provides for some type of alternative action to be taken in the lithographic process if bubbles are found to be present.

Turning to FIG. 8, methodology 800 begins by initializing the system operating characteristics to their starting values at 810. This can include, for example, but is not limited to positioning a substrate with a known structure into the immersion medium at the proper location for exposure from an optical component and/or setting initial parameters of an incident beam for monitoring the immersion medium in accordance with an aspect of the present invention. An expected optical signature for the known structure of the substrate in the immersion medium under desired conditions where no bubbles are present is made available in memory or a data store in accordance with another aspect of the present invention.

At 820, an incident beam is emitted from a light source of the bubble monitoring system. The emitted incident beam travels through the immersion medium toward the substrate so as to be incident on a known spot on the substrate and at a known incident angle to a normal. At 830, a reflected and/or diffracted beam(s) produced from the incident beam interacting with the substrate and with the immersion medium is detected. The reflected and/or diffracted beam(s) are collected by one or more optical detectors/spectrometers or other optical detection devices capable of determining properties of the reflected and/or diffracted beam(s). The reflected and/or diffracted beam(s) contains information indicative of the immersion medium traversed and of the structure of the substrate from which the beams are reflected and/or diffracted. This information can be analyzed to determine the presence of bubbles within the immersion medium.

At 840, the information contained in the reflected and/or diffracted beam is analyzed to determine optical properties and characteristics of the reflected and/or diffracted beam. The optical properties and characteristics can include, for example, wavelength, intensity, and phase of light received at various locations on the optical detectors. The combination of these optical characteristic and locations is used to generate an observed optical signature.

The expected optical signature reflective of an acceptable immersion medium where no bubbles are present exists in memory from initialization. Such expected optical signature may have been obtained through direct observation or through simulation and modeling. At 850, the methodology continues and the observed optical signature of the reflected and/or diffracted beam(s) is pattern matched against the expected optical signature. At 860 a determination is made as to whether bubbles have been detected based upon whether or not the observed optical signature matches the expected optical signature. If bubbles are detected (the observed signature and the expected signature do not match) then at 870 the lithographic process is altered. Alteration of the lithographic process can include, for example, waiting a fixed period of time, repositioning a substrate, changing the immersion medium, etc. After completion of the alteration, the methodology returns to 820 and proceeds.

However, if at 860 it is determined that no bubbles exist (the observed signature matches the expected signature), then the methodology continues on to 880. At 880, it is determined whether the desired volume of the immersion medium has been completely evaluated or not. If the entire volume has not been completely evaluated, then at 890, the detector component is reconfigured by the process control component to evaluate a different portion of the immersion medium. Such reconfiguration may include, for example, repositioning the light source to emit a beam at a different incident angle so as to cover a different portion of the immersion medium by traversing a different path through the immersion medium and repositioning the optical detectors to receive reflected and/or diffracted beams. Upon completion of the reconfiguration of the detector component, the methodology returns to 820 where an incident beam is again emitted from the reconfigured component.

If, however, at 880, if it is determined that the entire desired volume of the immersion medium has been evaluated, then at 898 the lithographic process continues as planned.

FIG. 9 is a flow diagram illustrating a methodology for carrying out another aspect of the present invention. In accordance with an aspect of the present invention, methodology 900 provides for determining the location of bubbles within an immersion medium, and then selecting an alternative action, based at least in part, upon the location of any bubbles.

Turning to FIG. 9, methodology 900 begins by initializing the system operating characteristics to their starting values at 902. This can include, for example, but is not limited to positioning a substrate with a known structure into an immersion medium at the proper location for exposure from a lithographic optical component and/or setting initial parameters of an incident beam for monitoring the immersion medium in accordance with an aspect of the present invention. In accordance with another aspect of the present invention, a set of expected optical signatures corresponding to the known structures at known spots on the substrate for the immersion medium under desired conditions where no bubbles are present is made available in a data store or other suitable memory. Similarly, a library of optical signatures corresponding to the presence of one or more bubbles at one or more locations for a particular spot on a particular substrate in a particular medium is made available in a data store or other suitable memory.

At 904, an incident beam is emitted from a light source of the bubble monitoring system. The emitted incident beam travels through the immersion medium toward a substrate so as to be incident on a known spot on the substrate at a known incident angle to a normal. At 906, reflected and/or diffracted beam(s) produced from the incident beam interacting with the substrate and with bubbles within the immersion medium are detected. The reflected and/or diffracted beam(s) are received by one or more optical detectors comprising spectrometers or other optical detection devices capable of determining properties of the reflected and/or diffracted beam(s). The reflected and/or diffracted beam(s) contains information indicative of the immersion medium traversed and of the structure of the substrate from which the beams are reflected and/or diffracted. This information can be analyzed to determine the presence of bubbles within the immersion medium.

At 908, the information contained in the reflected and/or diffracted beam(s) is analyzed to determine optical properties and characteristics of the reflected and/or diffracted beam(s). The optical properties and characteristics can include, for example, wavelength, intensity, and phase of light received at various locations on the detectors. The combination of these optical characteristic and locations is used to generate an observed optical signature.

An expected optical signature, reflective of an acceptable immersion medium where no bubbles are present, is available in memory or a data store from initialization. Such optical signature may be obtained through direct observation or through simulation and modeling. At 910, the methodology continues and the observed optical signature of the reflected and/or diffracted beam(s) is pattern matched against the expected optical signature.

At 912 a determination is made as to whether bubbles have been detected based upon whether or not the observed optical signature matches the expected optical signature. If at 912 it is determined that no bubbles exist (the observed signature matches the expected signature), the methodology continues on to 914. At 914, it is determined whether the desired volume of the immersion medium has been completely evaluated or not. If the entire volume of the immersion medium has not been completely evaluated, then at 916, the detector component is reconfigured by the process control component to evaluate a different portion of the immersion medium. Such reconfiguration may comprise, for example, repositioning the light source to emit a beam at a different incident angle so as to cover a different portion of the immersion medium by traversing a different path through the immersion medium and realigning, if necessary, the optical detectors to receive reflected and/or diffracted beam(s). Upon completion of the reconfiguration of the detector component, the methodology returns to 904 where an incident beam is again emitted from the reconfigured detector component.

If, however, at 914, if it is determined that the entire desired volume of the immersion medium has been evaluated, then at 918 the lithographic process continues as planned.

Returning to 912, if it is determined that bubbles are present in the immersion medium (the observed signature does not match the expected signature), then the methodology continues at 920 where the observed signature is pattern matched against a library of signatures corresponding to the presence or absence of one or more bubbles at various locations within the immersion medium for the known structure at the particular spot on the particular substrate. Based on the results of the pattern match, a determination is made at 922 as to whether the bubbles are located within an exposure beam path traversed by an exposure beam from the optical component (e.g. lens) to the substrate.

If at 922, it is determined based upon a pattern match that the bubbles do not lay within the exposure beam path, then the methodology proceeds to 914 and continues as described above. If, however, at 922 it is determined based upon a pattern match that the bubbles do lay within the exposure beam path, then at 924 the process control system alters the lithographic process. Alteration of the lithographic process can include waiting a fixed period of time, repositioning a substrate, changing the immersion medium, etc., and can be selected based upon the particular location of bubbles identified through the pattern match process. After completion of the alteration, the methodology returns to 904 and continues. If no pattern is matched at 922, it is determined that an unidentified condition of bubbles being present exists and the immersion lithographic process should not proceed without some type of corrective action, accordingly the methodology proceeds to 924 and proceeds as described above.

Although methodology 900 illustrated determining whether bubbles exist within a particular exposure path within the immersion medium, it is understood that the methodology may be applied to determine the presence of bubbles at any desired location of interest within the immersion medium.

Figures 10, 11, 12:
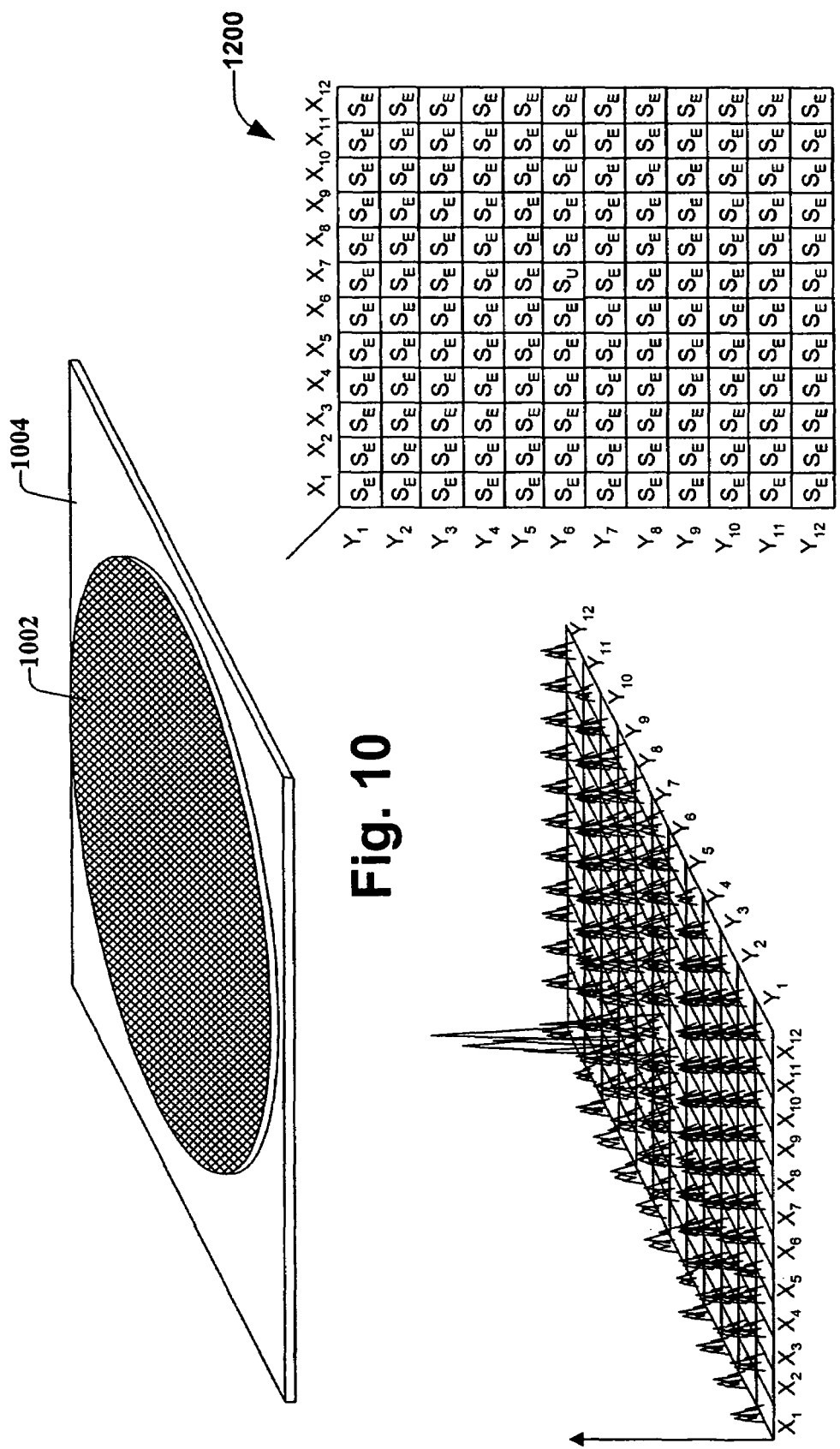
FIG. 10 illustrates a perspective view of a grid-mapped substrate in accordance with one or more aspects of the present invention.
FIG. 11 illustrates plots of measurements taken at grid-mapped locations on a substrate in accordance with one or more aspects of the present invention.
FIG. 12 illustrates a table containing entries corresponding to results of a comparison of observed optical signatures to expected optical signatures at respective grid-mapped locations on a substrate in accordance with one or more aspects of the present invention.

In accordance with one or more aspects of the present invention, FIG. 10 illustrates how a substrate 1002 may be partitioned for purposes of examining an immersion medium in conjunction with specified spot on a specific substrate. In FIG. 10, substrate 1002, situated on a stage 1004, is logically partitioned into grid blocks. Each grid block (XY) of the grid pattern corresponds to a particular portion of substrate 1002 to be exposed in a lithographic process. The structure associated each grid block is a known structure. The immersion medium is evaluated separately before lithographic exposure of each grid block portion of substrate 1002 and a corresponding signature is determined and evaluated for each grid location (i.e. spot).

In FIG. 11, one or more portions of the immersion medium in proximity to respective portions of substrate grid blocks ($X_1Y_1 \ldots X_{12}, Y_{12}$) are evaluated by a bubble monitoring system for signatures using reflected and/or diffracted light and the illustrated known substrate structures. It is to be appreciated that although FIG. 11 illustrates a substrate partitioned into 144 grid block portions, the substrate may be partitioned into any suitable number of portions. Given a set of expected signatures, a bubble monitoring system can determine if bubbles exist near any of the substrate grid block locations. Similarly, the bubble monitoring system may generate feed forward information which can facilitate maintaining, terminating, and/or altering an immersion lithographic process based at least in part on the observed signatures.

FIG. 12 illustrates a table 1200 recorded with results from comparing an observed signature to an expected signature for the individual grid block locations. In table 1200, $S_E$ indicates that the observed signature matched the expected signature and $S_U$ indicates that the observed signature was unexpected and did not match the expected signature for the given grid block location. It can be seen that all the signatures are expected except a signature for grid block location $X_7Y_6$. The table of results can be analyzed for the presence or absence of bubbles in specific grid block locations.

Figure 13:
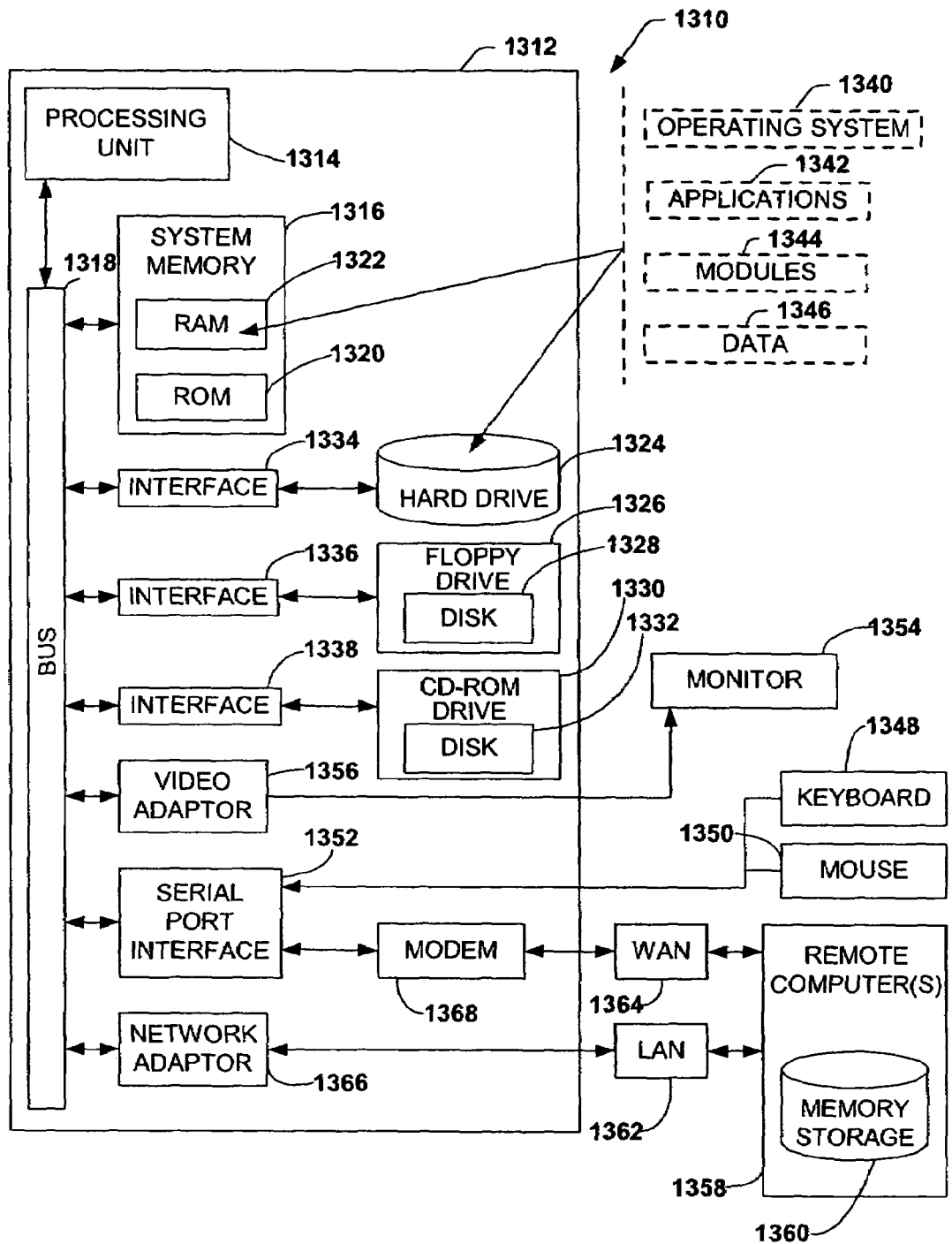
FIG. 13 is an illustration of an exemplary computing system and/or environment in connection with facilitating employment of the subject invention.

In order to provide additional context for various aspects of the present invention, FIG. 13 and the following discussion are intended to provide a brief, general description of a suitable computing environment 1310 in which the various aspects of the present invention can be implemented. While the invention has been described above in the general context of computer-executable instructions that may run on one or more computers, those skilled in the art will recognize that the invention also may be implemented in combination with other program modules and/or as a combination of hardware and software. Generally, program modules include routines, programs, components, data structures, etc. that perform particular tasks or implement particular abstract data types. Moreover, those skilled in the art will appreciate that the inventive methods may be practiced with other computer system configurations, including single-processor or multiprocessor computer systems, minicomputers, mainframe computers, as well as personal computers, hand-held computing devices, microprocessor-based or programmable consumer electronics, and the like, each of which may be operatively coupled to one or more associated devices. The illustrated aspects of the invention may also be practiced in distributed computing environments where certain tasks are performed by remote processing devices that are linked through a communications network. In a distributed computing environment, program modules may be located in both local and remote memory storage devices.

With reference to FIG. 13, an exemplary environment 1310 for implementing various aspects of the invention includes a computer 1312, including a processing unit 1314, a system memory 1316, and a system bus 1318 that couples various system components including the system memory to the processing unit 1314. The processing unit 1314 may be any of various commercially available processors. Dual microprocessors and other multi-processor architectures also can be used as the processing unit 1314.

The system bus 1318 can be any of several types of bus structure including a memory bus or memory controller, a peripheral bus, and a local bus using any of a variety of conventional bus architectures such as PCI, VESA, Microchannel, ISA, and EISA, to name a few. The system memory 1316 includes read only memory (ROM) 1320 and random access memory (RAM) 1322. A basic input/output system (BIOS), containing the basic routines that help to transfer information between elements within the computer 1312, such as during start-up, is stored in ROM 1320.

The computer 1312 further includes a hard disk drive 1324, a magnetic disk drive 1326 to read from or write to, for example, a removable disk 1328, and an optical disk drive 1330 for reading, for example, from a CD-ROM disk 1332 or to read from or write to other optical media. The hard disk drive 1324, magnetic disk drive 1326, and optical disk drive 1330 are connected to the system bus 1318 by a hard disk drive interface 1334, a magnetic disk drive interface 1336, and an optical drive interface 1338, respectively. The drives and their associated computer-readable media provide nonvolatile storage of data, data structures, computer-executable instructions, etc. for the computer 1312, including for the storage of broadcast programming in a suitable digital format. Although the description of computer-readable media above refers to a hard disk, a removable magnetic disk and a CD, it should be appreciated by those skilled in the art that other types of media which are readable by a computer, such as magnetic cassettes, flash memory cards, digital video disks, Bernoulli cartridges, and the like, may also be used in the exemplary operating environment, and further that any such media may contain computer-executable instructions for performing the methods of the present invention.

A number of program modules may be stored in the drives and RAM 1322, including an operating system 1340, one or more application programs 1342, other program modules 1344, and program data 1346. The operating system 1340 in the illustrated computer is, for example, the "Microsoft® Windows® NT" operating system, although it is to be appreciated that the present invention may be implemented with other operating systems or combinations of operating systems, such as UNIX®, LINUX® etc.

A user may enter commands and information into the computer 1312 through a keyboard 1348 and a pointing device, such as a mouse 1350. Other input devices (not shown) may include a microphone, an IR remote control, a joystick, a game pad, a satellite dish, a scanner, or the like. These and other input devices are often connected to the processing unit 1314 through a serial port interface 1352 that is coupled to the system bus 1318, but may be connected by other interfaces, such as a parallel port, a game port, a universal serial bus ("USB"), an IR interface, etc. A monitor 1354 or other type of display device is also connected to the system bus 1318 via an interface, such as a video adapter 1356. In addition to the monitor, a computer typically includes other peripheral output devices (not shown), such as speakers, printers, etc.

The computer 1312 may operate in a networked environment using logical connections to one or more remote computers, such as a remote computer(s) 1358. The remote computer(s) 1358 may be a workstation, a server computer, a router, a personal computer, microprocessor based entertainment appliance (e.g., a WEBTV® client system), a peer device or other common network node, and typically includes many or all of the elements described relative to the computer 1312, although, for purposes of brevity, only a memory storage device 1360 is illustrated. The logical connections depicted include a local area network (LAN) 1362 and a wide area network (WAN) 1364. Such networking environments are commonplace in offices, enterprise-wide computer networks, intranets and the Internet.

When used in a LAN networking environment, the computer 1312 is connected to the local network 1362 through a network interface or adapter 1366. When used in a WAN networking environment, the computer 1312 typically includes a modem 1368, or is connected to a communications server on the LAN, or has other means for establishing communications over the WAN 1364, such as the Internet. The modem 1368, which may be internal or external, is connected to the system bus 1318 via the serial port interface 1352 to enable communications, for example, via POTS. The modem 1368 may also, in an alternative embodiment, be connected to the network adaptor 1366 to enable communications, for example, via DSL or cable. In a networked environment, program modules depicted relative to the computer 1312, or portions thereof, will be stored in the remote memory storage device 1360. It may be appreciated that the network connections shown are exemplary and other means of establishing a communications link between the computers may be used.

Described above are preferred aspects of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications and variations that fall within the spirit and scope of the appended claims.

The invention claimed is:

1. A bubble monitoring system that facilitates determination of presence of one or more bubbles in an immersion medium comprising:
    a light source that projects an incident beam of light through the immersion medium to a substrate;
    a light detector that receives reflected and/or diffracted portions of the incident beam;
    a bubble monitoring component that determines or infers presence or absence of one or more bubbles in the immersion medium based in part on the light received by the detector; and
    a process control component that alters a lithographic process to mitigate presence of bubbles, the lithographic process is altered by at least one of causing the process to wait, or repositioning the substrate, or effecting removal and replacement of the immersion medium before proceeding with a next step in the immersion lithographic process.

2. The system of claim 1, the light source comprising at least one of a frequency stabilized laser, a laser diode, a helium neon gas laser, an excimer laser, a halogen lamp, a mercury lamp, an ultraviolet light source, and an extreme-ultraviolet light source.

3. The system of claim 1, the light detector comprising at least one of a photodetector, an array of photodetectors, and a spectrometer.

4. The system of claim 1 further comprising an artificial intelligence component that performs a probabilistic and/or statistical-based analysis in connection with inferring presence or absence of the bubbles.

5. The system of claim 1, the process control component causing the lithographic process to wait until the one or more bubbles are no longer present in the immersion medium.

6. The system of claim 1, the process control component causing the lithographic process to wait for a fixed period of time.

7. The system of claim 1, the immersion medium comprising water.

8. The system of claim 1, the immersion medium comprising oil.

9. The system of claim 1, the immersion medium is fully transparent to the incident beam of light and has a refractive index greater than 1 hence allowing for production of features with smaller critical dimensions.

10. A lithographic monitoring system comprising:
    means for determining presence of one or more bubbles in an immersion medium;
    means for altering an immersion lithographic process based at least in part on the presence of bubbles and
    means for repositioning a substrate;
    wherein the means for altering the lithographic process alters the immersion lithographic process by at least one of: causing the immersion lithographic process to wait until the one or more bubbles are no longer present in the immersion medium, or to wait a fixed period of time, or activating the means for repositioning the substrate, or effecting removal and replacement of the immersion medium before proceeding with a next step in the immersion lithographic process.

11. The system of claim 10, further comprising means for emitting an incident light beam through an immersion medium to a specific spot on a substrate that includes a known structure.

12. The system of claim 11, further comprising means for detecting at least one of reflected and diffracted light beams created as a result of one or more interactions of the incident light beam with the immersion medium and the substrate.

13. The system of claim 12, further comprising means for deriving an observed optical signature based upon a set of characteristics of the one or more reflected and diffracted lights.

14. The system of claim 13, further comprising means for comparing the observed optical signature to a library of optical signatures.

15. The system of claim 11, further comprising means for varying a time interval before a next step of the immersion lithographic process.

* * * * *